(12) United States Patent  
Yoshimura

(10) Patent No.: US 12,321,539 B2  
(45) Date of Patent: Jun. 3, 2025

(54) MEDICAL DEVICE

(71) Applicant: OLYMPUS CORPORATION, Tokyo (JP)

(72) Inventor: Takehiro Yoshimura, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 742 days.

(21) Appl. No.: 17/376,378

(22) Filed: Jul. 15, 2021

(65) Prior Publication Data

US 2021/0338048 A1 Nov. 4, 2021

Related U.S. Application Data

(63) Continuation of application No. PCT/JP2019/002376, filed on Jan. 24, 2019.

(51) Int. Cl.
*G06F 3/0354* (2013.01)
*A61B 1/00* (2006.01)
*A61B 1/01* (2006.01)
*A61B 5/00* (2006.01)
*G06F 3/0488* (2022.01)

(52) U.S. Cl.
CPC ............ *G06F 3/03547* (2013.01); *A61B 1/01* (2013.01); *A61B 5/7475* (2013.01); *G06F 3/0488* (2013.01); *A61B 1/00042* (2022.02)

(58) Field of Classification Search
CPC .... G06F 3/03547; G06F 3/0488; G06F 1/169; A61B 1/01; A61B 5/7475; A61B 1/00042; A61B 8/00
See application file for complete search history.

(56) References Cited

U.S. PATENT DOCUMENTS

| 4,762,227 | A | * | 8/1988 | Patterson | H05K 5/0017 206/778 |
|---|---|---|---|---|---|
| 5,499,713 | A | * | 3/1996 | Huffer | H01H 9/0242 206/320 |
| 5,812,188 | A | * | 9/1998 | Adair | A61B 1/00048 600/101 |
| 5,872,527 | A | | 2/1999 | Yanagisawa | |
| 9,459,656 | B2 | * | 10/2016 | Shai | G06F 1/1615 |

(Continued)

FOREIGN PATENT DOCUMENTS

| DE | 102012213322 A1 | * | 1/2014 | ............ A61B 46/10 |
|---|---|---|---|---|
| JP | H08-123595 A | | 5/1996 | |

(Continued)

OTHER PUBLICATIONS

International Search Report dated Apr. 9, 2019 issued in PCT/JP2019/002376.

(Continued)

*Primary Examiner* — Rufus C Point
(74) *Attorney, Agent, or Firm* — Scully, Scott, Murphy & Presser, P.C.

(57) ABSTRACT

A medical device includes: a main body in which an operation face meant for receiving input of position information from a user is formed on a principal face of the main body; a sheet configured to cover the operation face of the main body and cover an area from the principal face to a reverse face of the main body; and a guide that is installed on the reverse face, the guide being configured to hold the sheet in a slidable manner.

20 Claims, 5 Drawing Sheets

(56) References Cited

U.S. PATENT DOCUMENTS

| | | | |
|---|---|---|---|
| 2005/0073506 A1* | 4/2005 | Durso | G06F 1/1601 |
| | | | 345/173 |
| 2007/0247793 A1* | 10/2007 | Carnevali | G06F 1/1656 |
| | | | 361/679.1 |
| 2008/0302456 A1* | 12/2008 | Cook | A45C 11/00 |
| | | | 150/154 |
| 2012/0037536 A1* | 2/2012 | Lonsdale, II | G06F 1/1628 |
| | | | 206/701 |
| 2015/0104595 A1* | 4/2015 | Parrill | H04M 1/185 |
| | | | 428/36.5 |
| 2018/0059717 A1* | 3/2018 | Kim | G06F 3/1446 |
| 2018/0116356 A1* | 5/2018 | Richardson | H05K 5/0013 |
| 2018/0168303 A1* | 6/2018 | Marks | G06F 1/1628 |
| 2018/0214131 A1 | 8/2018 | Ryu et al. | |
| 2019/0254631 A1 | 8/2019 | Yoshimura | |

FOREIGN PATENT DOCUMENTS

| | | | | |
|---|---|---|---|---|
| JP | 2003-029905 A | | 1/2003 | |
| JP | 2007279437 A | * | 10/2007 | |
| JP | 2018-075190 A | | 5/2018 | |
| KR | 20110054722 A | * | 5/2011 | G06F 3/0447 |
| KR | 20160041659 A | * | 4/2016 | A45C 11/00 |

OTHER PUBLICATIONS

ITmedia [online], Dec. 21, 2012 [retrieved on Feb. 19, 2019] Internet <https://itmedia.co.jp/mobile/article/1212/21/news149.html>, with partial translation, cited in ISR.

* cited by examiner

MEDICAL DEVICE

CROSS-REFERENCE TO RELATED APPLICATION

This application is a continuation of International Application No. PCT/JP2019/002376, filed on Jan. 24, 2019, the entire contents of which are incorporated herein by reference.

BACKGROUND

1. Technical Field

The present disclosure is related to a medical device.

2. Related Art

In order to observe the characteristics of an observation target such as biological tissues or a biomaterial, sometimes an ultrasound image is used that is generated based on the ultrasound waves reflecting from the observation target. At the time of diagnosing the biological tissues in a body, an ultrasound endoscope is used in which an ultrasound transducer is installed at the front end of the insertion portion.

As a medical device involved in the task of observation performed using an ultrasound endoscope, conventionally a trackball is used. However, in recent years, from the perspective of cleanability, a touchpad is being used.

Moreover, from the perspective of cleanability, in the main body of a medical device, it is desirable to attach a sheet on the operation face having the touchpad installed thereon (for example, refer to Japanese Patent Application Laid-open No. 2018-75190). As a method of attaching a sheet on the operation face, it is common practice to form a depressed portion on the operation face and to attach a sheet on the inside of the depressed portion. In that case, in order to prevent a situation in which the main body and the sheet undergoes expansion or contraction due to the changes in temperature during transportation or during use and the sheet sags or comes off as a result, the depressed portion is formed to be slightly larger than the sheet. For that reason, a groove gets formed in between the inner wall face of the depressed portion and the edges of the sheet.

SUMMARY

In some embodiments, a medical device includes: a main body in which an operation face meant for receiving input of position information from a user is formed on a principal face of the main body; a sheet configured to cover the operation face of the main body and cover an area from the principal face to a reverse face of the main body; and a guide that is installed on the reverse face, the guide being configured to hold the sheet in a slidable manner.

In some embodiments, a medical device includes: a main body in which an operation face meant for receiving input of position information from a user is formed on a principal face of the main body; and a sheet configured to cover the operation face of the main body and cover an area from the principal face to a reverse face of the main body. Coefficient of thermal expansion of the main body is different from coefficient of thermal expansion of the sheet.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
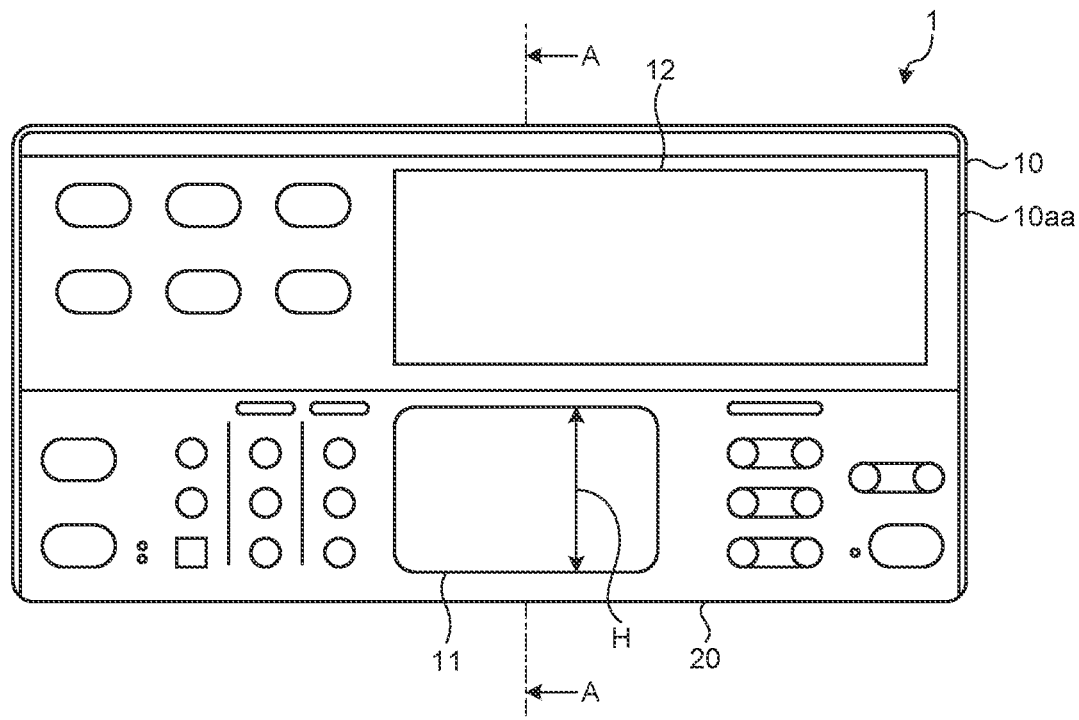
FIG. 1 is a schematic diagram illustrating a configuration of a medical device according to a first embodiment.

Exemplary embodiments of a medical device according to the disclosure are described below with reference to the accompanying drawings. However, the disclosure is not limited by the embodiments described below. Thus, the disclosure can be applied in general to a medical device in which the operation face of the main body is covered by a sheet.

Meanwhile, in the drawings, identical or corresponding elements are referred to by the same reference numerals. Moreover, each drawing is schematic in nature, and it needs to be kept in mind that the relationships among the dimensions of the elements or the ratio of the elements may be different than the actual situation. Among the drawings too, there may be portions having different relationships among the dimensions or having different ratios among the dimensions.

First Embodiment

Figure 2:
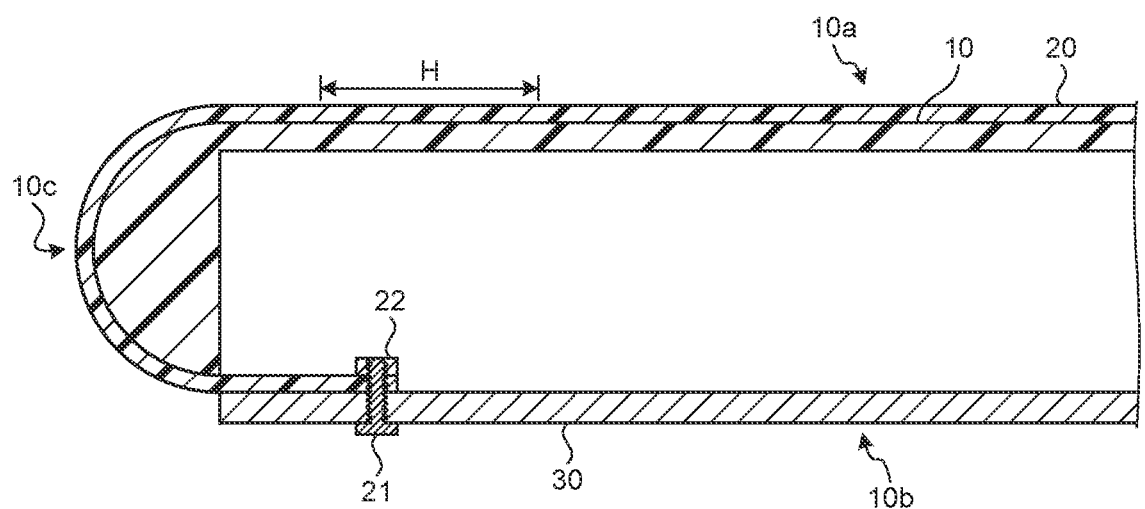
FIG. 2 is a cross-sectional view along A-A line illustrated in the medical device in FIG. 1.

FIG. 1 is a schematic diagram illustrating a configuration of a medical device according to a first embodiment. FIG. 2 is a cross-sectional view along A-A line illustrated in the medical device in FIG. 1. As illustrated in FIGS. 1 and 2, a medical device 1 according to the first embodiment includes a main body 10; a sheet 20 that covers an operation face 10aa of the main body 10; and a base plate 30 that covers a reverse face 10b of the main body 10. In the following explanation, in the main body 10, the face on which the operation face 10aa is formed is treated as a principal face 10a; the face on the opposite side of the principal face 10a is treated as the reverse face 10b; and the face connecting the principal face 10a and the reverse face 10b is treated as a side face 10c.

The main body 10 includes a touchpad 11 that receives an input about position information from the user; and includes a display unit 12 that is capable of displaying a variety of information. The main body 10 is made of, for example, a resin such as ABS resin. In the vicinity of the touchpad 11 of the main body 10, the side face 10c that connects the principal face 10a and the reverse face 10b is a curved surface. As illustrated in FIG. 1, the touchpad 11 has a width H in the height direction (i.e., the vertical direction with reference to FIG. 1), and is installed at the position as illustrated in FIG. 2 that is a cross-sectional view along line A-A.

The touchpad 11 is configured using a contact sensor. When a contacting object such as a finger of the operator makes a contact with the touch sensor, the touch sensor detects and outputs the contact position. While the contacting object remains in contact with the contact sensor, the touchpad 11 repeatedly detects the contact position and repeatedly outputs the contact position that changes with time.

The display unit 12 is configured using a display panel made of liquid crystals or organic EL (Electro Luminescence). Alternatively, the display unit 12 can be configured using a touch-sensitive panel capable of receiving user input.

The sheet 20 covers an area from the principal face 10a to the reverse face 10b on one side present close to the touchpad 11. That is, the sheet 20 covers the side face 10c that is a curved surface. The sheet 20 is made of, for example, a resin such as PET resin. Thus, the sheet 20 has a smaller coefficient of thermal expansion than the coefficient of thermal expansion of the main body 10. Hence, the thermal expansion or the thermal contraction of the sheet 20 is smaller than the thermal expansion or the thermal contraction of the main body 10.

Of the sheet 20, the end of the portion extending up to the reverse face 10b is sandwiched between the main body 10 and the base plate 30. That end of the sheet 20 is fixed to the base plate 30 using a screw 21 inserted through a hole formed on the sheet 20, and using a bolt 22 into which the screw 21 is screwed.

The base plate 30 is fixed to the main body using a screw (not illustrated). The base plate 30 is made of a metal or an alloy. Thus, the coefficient of thermal expansion of the base plate 30 is sufficiently smaller than the coefficients of thermal expansion of the main body 10 and the sheet 20. Hence, the thermal expansion or the thermal contraction of the base plate 30 is negligibly smaller than the thermal expansion or the thermal contraction of the main body 10 and the sheet 20.

As explained above, according to the first embodiment, in the vicinity of the touchpad 11, the sheet 20 covers the area from the principal face 10a to the reverse face 10b of the main body 10. As a result, in the vicinity of the touchpad 11, since no groove is formed in between the main body 10 and the sheet 20, the situation of having a dirty groove is prevented and hence a need to clean the groove does not arise. That is, the medical device 1 has good cleanability.

In the first embodiment, the explanation is given about an example in which the sheet 20 covers the entire area from the principal face 10a to the reverse face 10b on the one side present close to the touchpad 11. However, that is not the only possible case. Alternatively, for example, of the one side present close to the touchpad 11, the sheet 20 can cover, from the principal face 10a to the reverse face 10b, only the area close to the touchpad 11. In that case too, since there is no groove in the vicinity of the touchpad 11, good cleanability is achieved.

Moreover, in the first embodiment, the explanation is given about the example in which the entire side face 10c of the main body 10 is a curved surface. However, that is not the only possible case. Alternatively, for example, of the side face 10c of the main body 10, only some portion in the vicinity of the touchpad 11 can be a curved surface.

Furthermore, in the first embodiment, the explanation is given about an example in which the sheet 20 covers the entire side face 10c that is a curved surface. However, that is not the only possible case. Alternatively, for example, the sheet 20 can cover at least part of the side face 10c that is a curved surface, the at least part of the side face 10c being in the vicinity of the touchpad 11.

Moreover, in the first embodiment, the explanation is given about an example in which the side face 10c is a curved surface. However, that is not the only possible case. That is, there is no particular restriction on the shape of the side face 10c. For example, the side face 10c can be made of an orthogonal portion that is orthogonal to the principal face 10a and the reverse face 10b, and a chamfered portion that is connected to the principal face 10a and the reverse face 10b from above and below of the orthogonal portion and that intersects with the orthogonal portion and the principal face 10a or the reverse face 10b.

Second Embodiment

Figure 3:
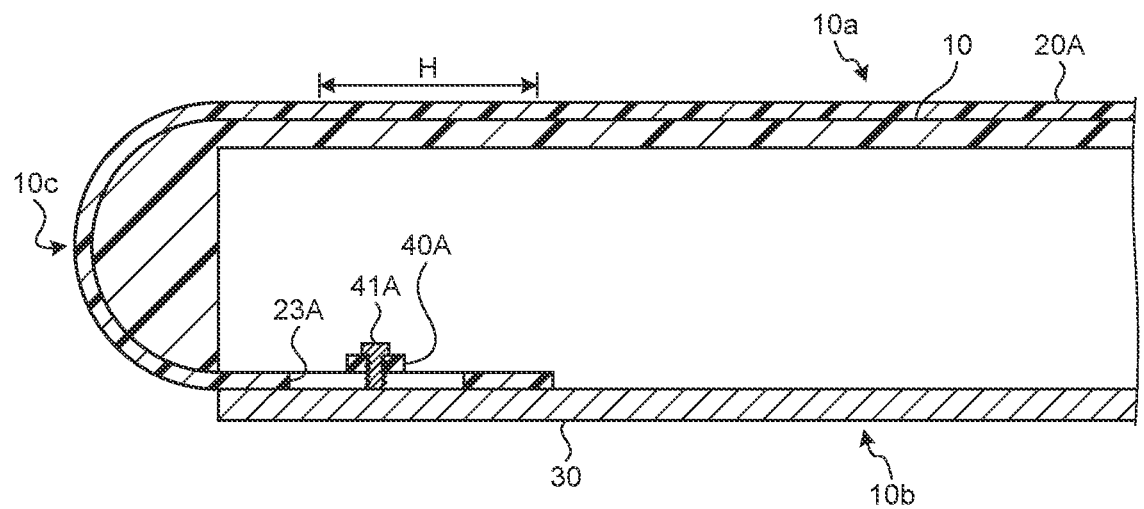
FIG. 3 is a cross-sectional view illustrating a configuration of a medical device according to a second embodiment.

FIG. 3 is a cross-sectional view illustrating a configuration of a medical device according to a second embodiment. As illustrated in FIG. 3, the medical device according to the second embodiment includes a guide 40A that holds a sheet 20A in a slidable manner between the main body 10 and the base plate 30; and includes screws 41A that are screwed to the guide 40A and that are inserted through long holes 23A formed in the sheet 20A.

Figure 4:
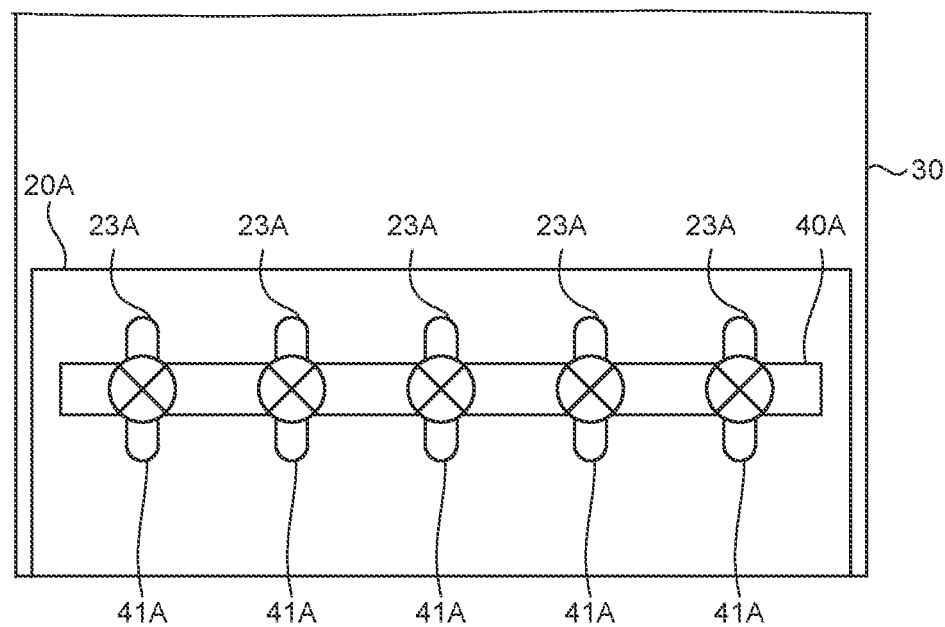
FIG. 4 is a diagram in which a base plate and a guide illustrated in FIG. 3 are viewed from the principal face side.

FIG. 4 is a diagram in which the base plate and the guide illustrated in FIG. 3 are viewed from the principal face side. In FIG. 4, the main body 10 is not illustrated. Moreover, the left and right directions with reference to FIG. 4 correspond to the left and right directions with reference to FIG. 1. As illustrated in FIG. 4, the long holes 23A have the shape of long holes extending along the direction in which the sheet 20A extends from the principal face 10a to the reverse face 10b.

The guide 40A has an elongated shape along the direction parallel to the side on which the curved surface of the main body 10 is formed. The guide 40A is fixed to the main body 10 via a substrate (not illustrated).

Given below is the explanation of the case in which the main body 10 and the sheet 20A undergo expansion or contraction due to the changes in temperature during transportation or during use. When a medical device is transported in an airplane, the midair environment in which the medical device is kept has extremely low temperatures. On the other hand, when a medical device is transported in a vehicle by road, the environment in which the medical device is kept sometimes has extremely low temperatures or extremely high temperatures depending on the climate and the weather. Moreover, when a medical device is in use, the heat generated by the display unit 12 sometimes causes heating of the medical device. Conventionally, when a medical device becomes cold or hot, since the coefficient of thermal expansion of the main body is different from the coefficient of thermal expansion of the sheet, sometimes the sheet sags or comes off from the main body.

Figure 5:
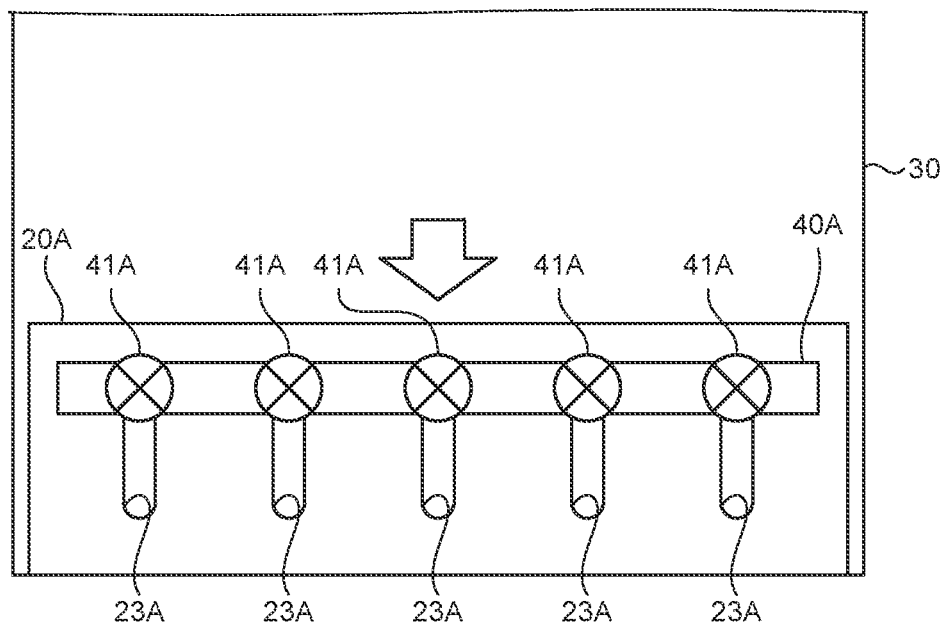
FIG. 5 is a diagram illustrating the state of a sheet when a main body undergoes expansion.

FIG. 5 is a diagram illustrating the state of the sheet when the main body undergoes expansion. As illustrated in FIG. 5, when the main body 10 and the sheet 20A undergo expansion, since the main body 10 has a greater coefficient of expansion than the sheet 20A, the sheet 20A gets pulled toward the side face 10c. At that time, since the sheet 20A slides while being held by the guide 40A, the sheet 20A is prevented from sagging or coming off from the main body 10.

Figure 6:
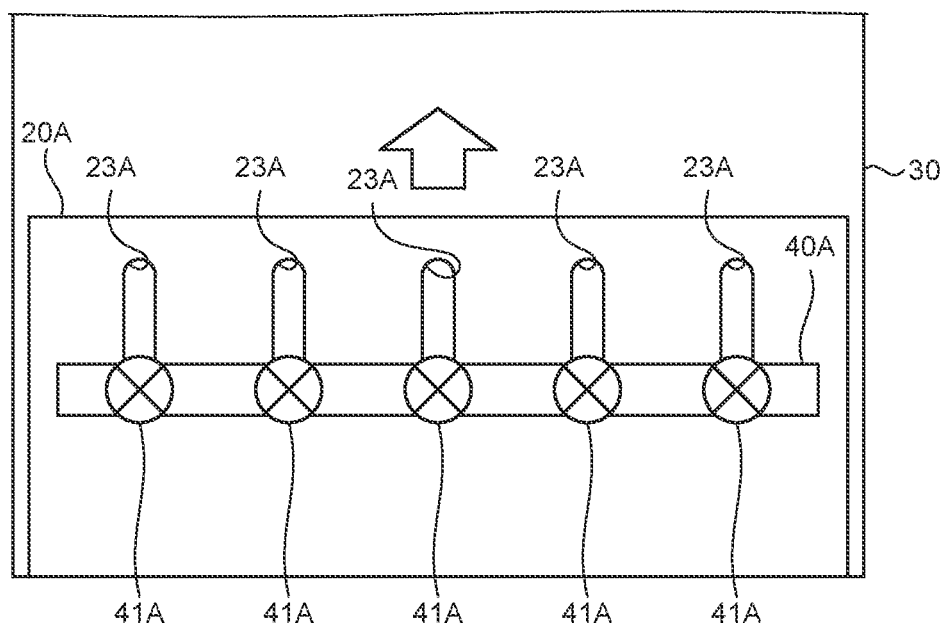
FIG. 6 is a diagram illustrating the state of the sheet when the main body undergoes contraction.

FIG. 6 is a diagram illustrating the state of the sheet when the main body undergoes contraction. As illustrated in FIG. 6, when the main body 10 and the sheet 20A undergo contraction, since the main body 10 has a greater coefficient of expansion than the sheet 20A, the sheet 20A gets pressed in the direction away from the side face 10*c*. At that time, since the sheet 20A slides while being held by the guide 40A, the sheet 20A is prevented from sagging or coming off from the main body 10.

As explained above, according to the second embodiment, since the edges of the sheet 20A are held in a slidable manner by the guide 40A, the sheet 20A is prevented from sagging or coming off from the main body 10 under low temperature or under high temperature.

Modification Example 2-1

Figure 7:
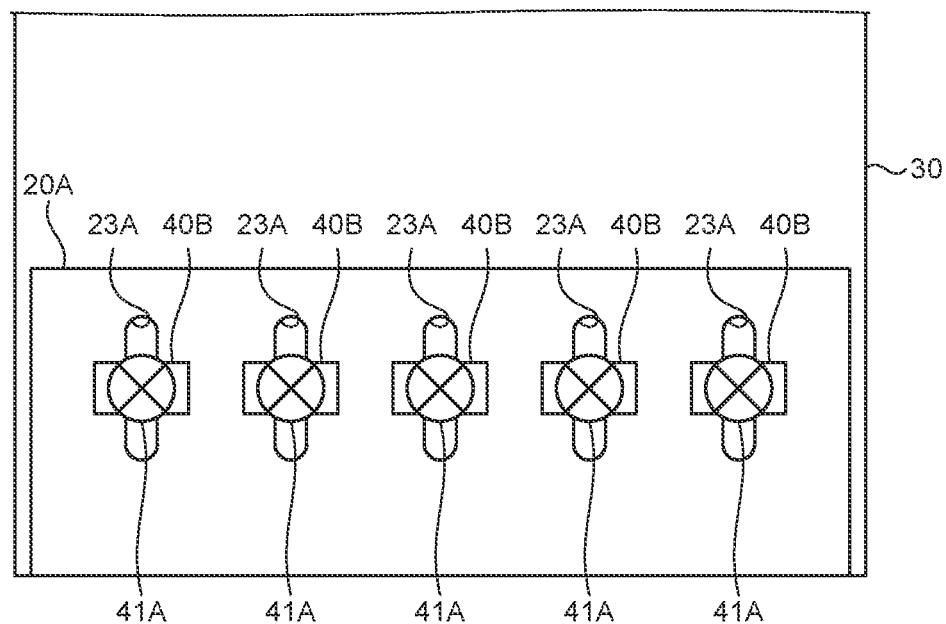
FIG. 7 is a schematic diagram illustrating a configuration of a medical device according to a modification example 2-1.

FIG. 7 is a schematic diagram illustrating a configuration of a medical device according to a modification example 2-1. As illustrated in FIG. 7, in the medical device according to the modification example 2-1, a guide 40B is partitioned into a plurality of guides 40B along the direction parallel to the side on which the curved surface of the main body 10 is formed. In this way, as long as the guide is configured to hold the sheet in a slidable manner, there is no particular restriction on the shape of the guide.

Modification Example 2-2

Figure 8:
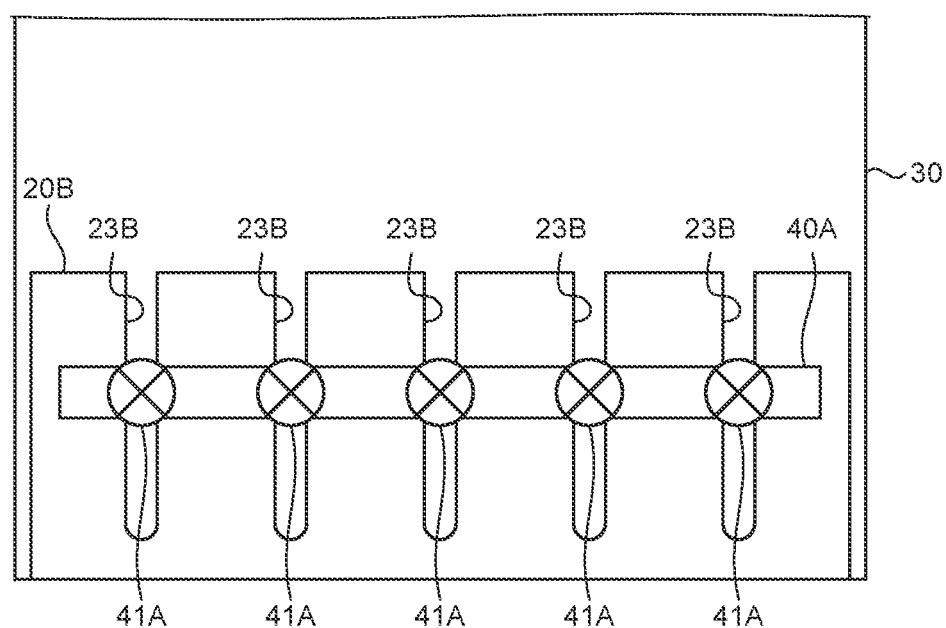
FIG. 8 is a schematic diagram illustrating a configuration of a medical device according to a modification example 2-2.

FIG. 8 is a schematic diagram illustrating a configuration of a medical device according to a modification example 2-2. As illustrated in FIG. 8, in the medical device according to the modification example 2-2, a sheet 20B includes grooves 23B that extend up to the edges of the sheet 20B along the direction in which the sheet 20B extends from the principal face to the reverse face. In this way, as long as the sheet has notches such as long holes or grooves that enable sliding with respect to the screws 41A, there is no particular restriction on the shape of the notches.

Third Embodiment

Figure 9:
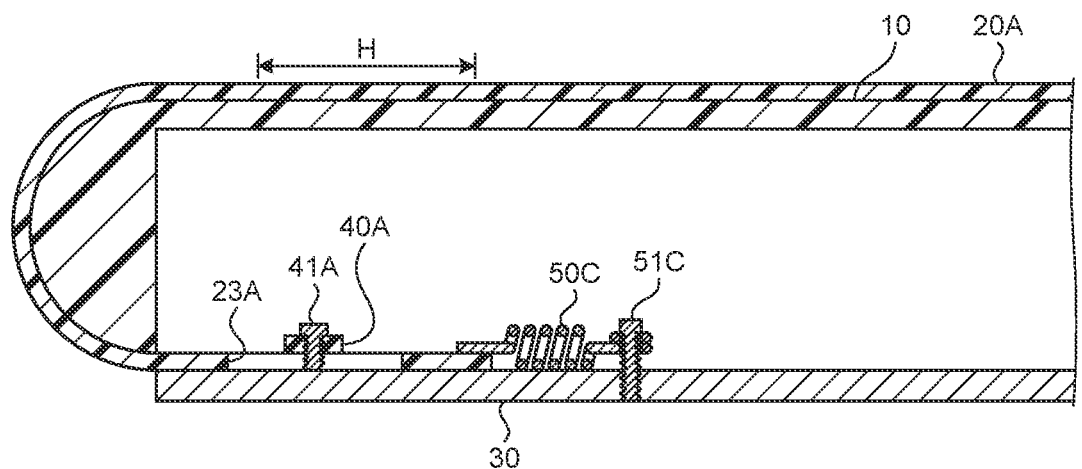
FIG. 9 is a cross-sectional view illustrating a configuration of a medical device according to a third embodiment.

FIG. 9 is a cross-sectional view illustrating a configuration of a medical device according to a third embodiment. As illustrated in FIG. 9, the medical device according to the third embodiment includes a spring 50C that has one end fixed to the sheet 20A and that pulls the end of the sheet 20A along the direction in which the sheet 20A extends from the principal face to the reverse face; and a screw 51C that is used for fixing the other end of the spring 50C to the base plate 30. When the main body 10 and the sheet 20A undergo thermal contraction, the spring 50C pulls the end of the sheet 20A, so that the sheet 20A slides in between the main body 10 and the base plate 30. As a result, the sheet 20A is prevented from sagging or coming off from the main body 10.

Meanwhile, the configuration for pulling the end of the sheet 20A is not limited to the spring 50C. Alternatively, for example, the end of the sheet 20A can be rounded like a roll while being fixed to a shaft, and the shaft can be rotated so that that the sheet 20A gets rolled up. With that, the sheet 20 can be made to slide.

According to the disclosure, it becomes possible to implement a medical device having good cleanability.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical device comprising:
a casing having an interior cavity, the casing comprising:
a first surface including an input portion configured to receive an input from a user;
a second surface opposed the first surface; and
a third surface connecting the first surface to the second surface, the first, second and third surfaces surrounding the interior cavity;
a sheet comprising:
a first sheet portion at least partially covering the first surface including the input portion;
a second sheet portion at least partially covering the second surface; and
a third sheet portion connecting the first sheet portion to the second sheet portion and at least partially covering the third surface; and
a projection extending from the second surface for slidably holding the second sheet portion relative to the second surface in a direction towards or away from the third sheet portion while the first sheet portion contacts the input portion;
wherein the first sheet portion is configured to transmit the input from the user through the first sheet portion such that the input is received by the input portion.

2. The medical device according to claim 1, wherein the input portion comprises a touchpad.

3. The medical device according to claim 1, wherein the third surface includes a curved surface.

4. The medical device according to claim 1, further comprising a base plate having the second surface, wherein the second sheet portion is internal to the interior cavity; and
the projection is provided in the interior of the cavity.

5. The medical device according to claim 4, wherein the second sheet portion comprises a slot elongated in the direction towards or away from the third sheet portion, the projection being disposed in the slot and fastened to the base plate to slidably hold the sheet on the base plate at the interior cavity.

6. The medical device according to claim 1, wherein a coefficient of thermal expansion of the casing is different from a coefficient of thermal expansion of the sheet such that the second sheet portion expands to slide relative to the second surface in the direction towards or away from the third sheet portion.

7. The medical device according to claim 6, wherein the sheet including a hole, the projection being inserted in the hole and connected to the second surface to fix a portion of the second sheet portion to the second surface.

8. The medical device according to claim 1, wherein the third sheet portion is configured to slide toward the third surface to cover a part of the third surface.

9. The medical device according to claim 8, wherein the first sheet portion is configured to slide toward or away from the third surface to cover the part of the third surface.

10. The medical device according to claim 1, wherein
the second sheet portion further comprising a slot elongated in the direction towards or away from the third sheet portion, and
the projection is connected to the second surface and disposed in the slot.

11. The medical device according to claim 10, wherein
the projection further comprising a guide having a width in a guiding direction orthogonal to the direction that is greater than a width of the slot in the guiding direction; and
the slot comprises a plurality of linear slots.

12. The medical device according to claim 1, wherein the projection comprises a plurality of projections, each disposed at the second surface and each independently slidably holding the second sheet portion relative to the second surface in the direction towards or away from the third sheet portion.

13. The medical device according to claim 1, further comprising an elastic material configured to bias the second sheet portion in a direction away from the third surface.

14. The medical device according to claim 1, wherein the second sheet portion is configured to slide along the second surface in the direction.

15. The medical device according to claim 1, wherein the first sheet portion is disposed against the first surface while the second sheet portion slides on the second surface.

16. A medical device comprising: a casing having an interior cavity, the casing comprising: a first surface including an input portion configured to receive an input from a user; and a second surface opposed the first surface; and a sheet at least partially covering the first surface including the input portion and at least partially covering the second surface, wherein a coefficient of thermal expansion of the casing is different from a coefficient of thermal expansion of the sheet such that a portion of the sheet covering the second surface slides relative to the second surface in a direction towards or away from a portion of the sheet covering the first surface while a first sheet portion contacts the input portion; wherein the first sheet portion is configured to transmit the input from the user through the first sheet portion such that the input is received by the input portion.

17. The medical device according to claim 16, wherein
the sheet further at least partially covering a third surface of the casing, the third surface connecting the first surface to the second surface, the first, second and third surfaces surrounding the interior cavity, and
a portion of the sheet covering the third surface slides relative to the second surface in a direction towards or away from the portions of the sheet covering the first surface and the second surface.

18. The medical device according to claim 16, wherein
the second sheet surface is in an interior of the casing; and
the casing having an opening through which the second portion of the sheet enters the interior of the casing.

19. A medical device comprising:
a casing having an interior cavity, the casing comprising:
a first surface including an input portion configured to receive an input from a user;
a second surface opposed the first surface; and
a third surface connecting the first surface to the second surface, the first, second and third surfaces surrounding the interior cavity; and
a sheet comprising:
a first sheet portion at least partially covering the first surface including the input portion;
a second sheet portion at least partially covering the second surface; and
a third sheet portion connecting the first sheet portion to the second sheet portion and at least partially covering the third surface;
wherein the second sheet portion being slidable relative to the second surface in a direction towards or away from the third sheet portion while the first sheet portion contacts the input portion;
wherein the first sheet portion is configured to transmit the input from the user through the first sheet portion such that the input is received by the input portion.

20. The medical device according to claim 19, further comprising a projection disposed at the second surface for slidably holding the second sheet portion relative to the second surface in the direction towards or away from the third sheet portion.

* * * * *